US00PP08690P

United States Patent [19]

Williams

[11] Patent Number: Plant 8,690

[45] Date of Patent: Apr. 19, 1994

[54] MINIATURE ROSE PLANT NAMED 'MICDEB'

[76] Inventor: Michael C. Williams, P.O. Box 203, Cross Hill, S.C. 29332

[21] Appl. No.: 994,502

[22] Filed: Dec. 21, 1992

[51] Int. Cl.[5] ..... A01H 5/00

[52] U.S. Cl. ..... Plt./7.1

[58] Field of Search ..... Plt. 7.1, 22

*Primary Examiner*—Howard J. Locker
*Assistant Examiner*—Elizabeth C. Kemmerer

[57] ABSTRACT

A new and distinct variety of miniature rose characterized by magenta buds and blooms of good form and a medium sized, upright plant with dark green semi-glossy foliage.

1 Drawing Sheet

BACKGROUND OF NEW VARIETY

The present introduction of a new and distinct variety of rose plant of the miniature rose class, which was created by my crossing as seed parent the floribunda rose named "Jazz Fest" (U.S. Plant Pat. No. 3,323) and as pollen parent the miniature rose named "Party Girl" (U.S. Plant Pat. No. 4,598), has the varietal denomination of "Micdeb".

Among the distinguishing characteristics possessed by this new variety which separate it from its parents and all other varieties of which I am aware are abundant magenta colored buds and blooms with long lasting flowers usually borne singly and a vigorous medium plant size with glossy greenish-purple new foliage.

The present variety of miniature rose was originated by me in Laurens County, S.C. Asexual reproduction by cuttings of the new variety as performed by me in Laurens County, S.C., has shown conclusively that the foregoing and other distinguishing characteristics come true to form and are established and faithfully transmitted through succeeding propogations.

BRIEF DESCRIPTION OF PHOTOGRAPH

The accompanying photograph shows typical specimens of the vegetative growth and flowers of the new variety in different stages of development and as depicted in color as nearly true as it is reasonably possible to make the same in a color photograph of this character.

DETAILED BOTANICAL DESCRIPTION OF NEW VARIETY

The following is a detailed description of my new rose variety, with color terminology in accordance with the plate numbers of The Royal Horticultural Society Colour Chart except where common dictionary terms of color definitions are employed.

Breeding: Seedling.

*Seed parent.*—Jazz Fest (U.S. Plant Pat. No. 3,323).

*Pollen parent.*—Party Girl (U.S. Plant Pat. No. 4,598).

Class: Miniature rose.

Variety: Micdeb.

Commercial Synonym: Debidue.

The following observations were made from specimens grown outdoors in Laurens County, S.C., U.S.A., in August, 1992.

FLOWER

Blooming habit: Recurrent.

A. Bud:

(1) *Size.*—Medium.

(2) *Form.*—Pear shaped.

(3) *Color.*—As sepals first divide: 71C with 155B base. As petals begin to unfurl: 71C with 155B base. As half-blown: inside and reverse of petals 71C-71D with 155B base.

(4) *Sepals.*—Thin, pointed, slightly longer than the petals.

(5) *Peduncle.*—Length: 1¼ inches. Aspect: mildly rough. Strength: erect, stable. Color: 137C.

B. Bloom:

(1) *Size.*—Average size when fully expanded: 1½ inches.

(2) *Borne.*—Singly, one to a stem and occasionally in sprays of 3 to 5 side buds.

(3) *Form.*—High centered until ½ open, becoming flat, with petals somewhat ruffled at maturity.

(4) *Petalage.*—Number under normal conditions is about 25.

(5) *Color.*—During first two days: Inner petals at center of flower: 71C. Outer petals: 71C. Base of petals (point of attachment): 155B. Reverse of petals: 71C. General tonality from a distance: 71C.

(6) *Color change.*—As bloom ages: 71C to 71D. General tonality: 71C. After three or more days: 71C.

C. Petals:

(1) *Texture.*—Slightly thick.

(2) *Appearance.*—Inside-velvety, outside-slightly satiny.

(3) *Form.*—Tear drop.

(4) *Arrangement.*—Regularly arranged.

(5) *Petaloids in center:* 3 to 5.

(6) *Persistence.*—Drop about 10 days after bloom is fully open.

(7) *Fragrance.*—No fragrance.

(8) *Lasting quality.*—Under normal conditions of sunlight and temperature, blooms last for 3–5 days.

REPRODUCTIVE ORGANS

A. Stamen, filaments and anthers:
(1) *Arrangement.*—Regularly arranged around styles.
(2) *Color.*—5C.

B. Pollen:
*Color.*—21A.

C. Styles: Uneven length, tightly bunched.

D. Stigmas:
*Color.*—17C.

E. Hips:
*Shape.*—Relatively round.
*Size.*—½ inch diameter.
*Color.*—40C when mature.
*Occasional seed protrusion.*

PLANT

A. Form: Upright.

B. Growth: Very vigorous.
*Height attained.*—Average of 24 inches.

C. Foliage: 5 to 7 leaflets.
(1) *Size.*—Medium.
(2) *Quantity.*—Abundant.
(3) *Color.*—New foliage: upper side: blend of 146B and 59A. under size: blend of 148C and 59A. Old foliage: upper side: 137A. under side: 148B.
(4) *Shape.*—Oval pointed.
(5) *Texture.*—Upper side: smooth with veins somewhat indented. Under side: raised veins, prickles on leaf stem.
(6) *Edge.*—Serrated.

(7) *Serration.*—Uniform indentations.
(8) *Leaf stem: Color: blend of* 144B and 59B. Under side: 145B.
(9) *Stipules.*—Slightly bearded, somewhat long.
(10) *Resistance to disease.*—Blackspot: good. Mildew: good. Rust: good.

D. Wood.
(1) *New wood.*—Color: 59B. Bark: Smooth.
(2) *Old wood.*—Color: 144A. Bark: Smooth.

E. Thorns:
*Quantity.*—Few on main stalks from base; very few on laterals from stalk.
*Form.*—Flat base, straight.
*Length.*—Mostly small.
*Color.*—59A.
*Position.*—Irregular.
*Prickles.*—Quantity: few on main stalks from base; none on laterals.

F. Winter hardiness: Protection is needed below 10 degrees Fahrenheit; can mound canes with soil or leaves for extra protection.

I claim:

1. A new and distinct variety of rose plant of the miniature rose class, substantially as herein shown and described, characterized particularly by blooms of reddish-purple coloring, with slightly thick petals, borne freely on an upright plant with glossy greenish-purple new foliage and semi-glossy medium green old foliage said plant being easy to propagate from cuttings, and said blooms being long-lasting on the plant and as cut flowers.

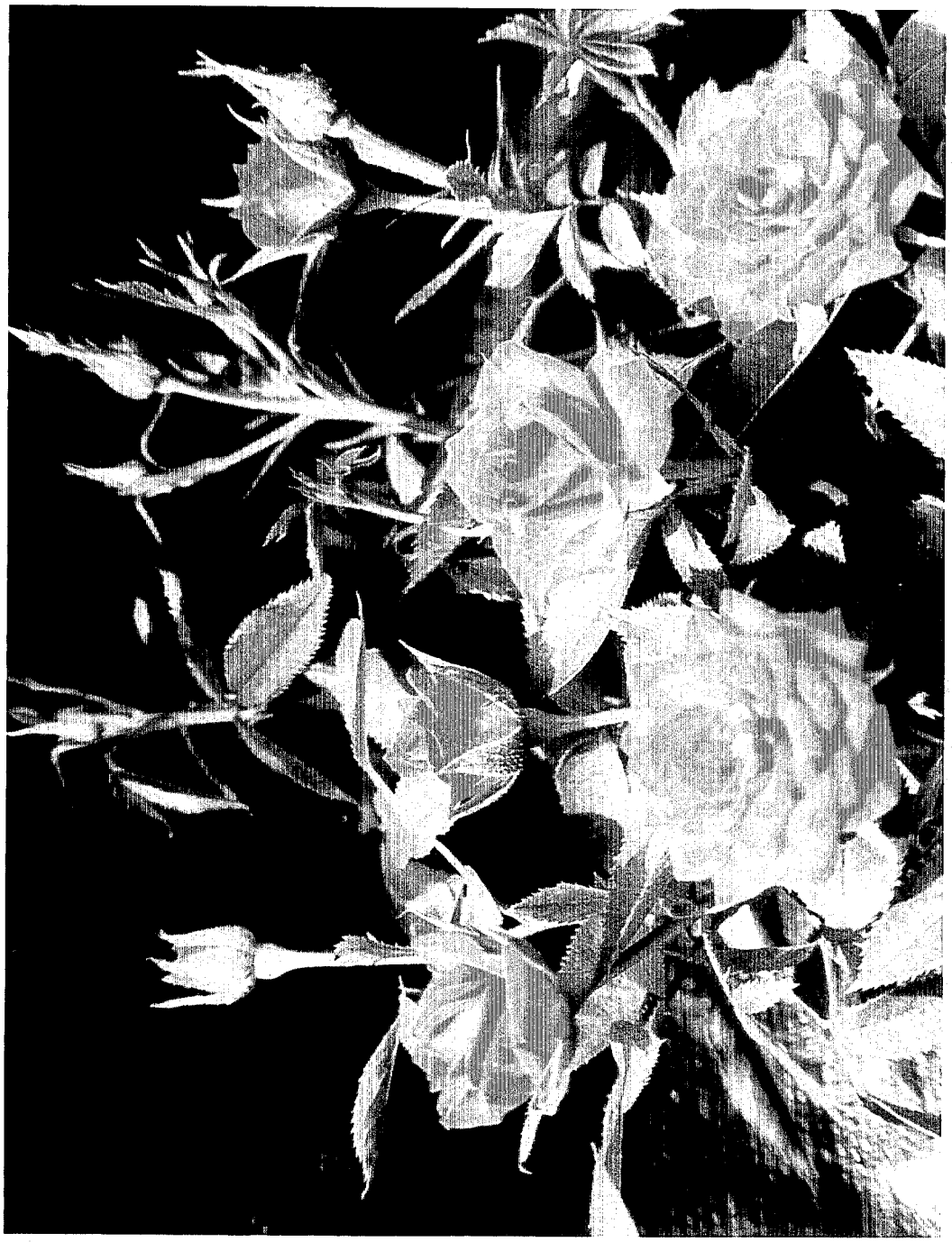

* * * * *